United States Patent
Farhan et al.

(10) Patent No.: US 7,772,965 B2
(45) Date of Patent: Aug. 10, 2010

(54) REMOTE WELLNESS MONITORING SYSTEM WITH UNIVERSALLY ACCESSIBLE INTERFACE

(76) Inventors: Fariborz M. Farhan, 135 Autry Landing Way, Alphretta, GA (US) 30022; John W. Peifer, 208 Rumson Rd., Atlanta, GA (US) 30305

( * ) Notice: Subject to any disclaimer, the term of this patent is extended or adjusted under 35 U.S.C. 154(b) by 0 days.

(21) Appl. No.: 11/835,405

(22) Filed: Aug. 7, 2007

(65) Prior Publication Data
US 2008/0033256 A1 Feb. 7, 2008

Related U.S. Application Data

(60) Provisional application No. 60/821,585, filed on Aug. 7, 2006, provisional application No. 60/939,432, filed on May 22, 2007.

(51) Int. Cl.
*G08B 5/22* (2006.01)
(52) U.S. Cl. ............ 340/286.07; 128/903; 340/539.12; 340/552; 340/561; 340/565; 340/573.1; 600/300
(58) Field of Classification Search ............... 600/300, 600/301; 128/903–905, 920; 340/552, 561, 340/565, 573.1, 286.07, 539.12
See application file for complete search history.

(56) References Cited

U.S. PATENT DOCUMENTS

| | | | |
|---|---|---|---|
| 5,558,638 A | 9/1996 | Evers et al. | |
| 5,610,590 A | 3/1997 | Johnson et al. | |
| 5,959,529 A | 9/1999 | Kail, IV | |
| 6,160,478 A | 12/2000 | Jacobsen et al. | |
| 6,265,972 B1 * | 7/2001 | Lee | 340/541 |
| 6,445,298 B1 * | 9/2002 | Shepher | 340/573.1 |
| 6,475,161 B2 * | 11/2002 | Teicher et al. | 600/558 |
| 6,611,206 B2 | 8/2003 | Eshelman et al. | |
| 7,002,463 B2 | 2/2006 | Wakabayashi | |
| 2002/0032470 A1 | 3/2002 | Linberg | |
| 2002/0082665 A1 | 6/2002 | Haller et al. | |
| 2003/0130590 A1 | 7/2003 | Bui et al. | |
| 2004/0130446 A1 | 7/2004 | Chen et al. | |
| 2004/0249250 A1 | 12/2004 | McGee et al. | |
| 2006/0154642 A1 | 7/2006 | Scannell, Jr. | |

* cited by examiner

*Primary Examiner*—Brent Swarthout
(74) *Attorney, Agent, or Firm*—Smith Frohwein Tempel Greenlee Blaha, LLC; Gregory Scott Smith

(57) ABSTRACT

A remote wellness monitoring system with universally accessible interface consists of an apparatus or home appliance unit running an embedded software program connected to a server computer via a phone line or high-speed internet. At home, the apparatus communicates with an optional set of medical health monitoring devices using wired or wireless communications methods in order to perform wellness measurements. Embodiments of the invention provide a novel user interface on the home appliance to make the system accessible to people with disabilities. The simple user interface is designed to be accessible to people who are blind or deaf or people who cannot use their hands and require an alternative interface device such as a sip & puff controller. The home unit can further monitor wellness activity of the care recipient by pegging the number of times the care recipient passes by an infra-red motion sensor.

4 Claims, 16 Drawing Sheets

REMOTE WELLNESS MONITORING SYSTEM WITH UNIVERSALLY ACCESSIBLE INTERFACE

CROSS-REFERENCE TO RELATED APPLICATIONS

This application is related to and claims the benefit of Provisional U.S. patent application No. 60/821,585 filed by Farhan on Aug. 7, 2006 and also Provisional U.S. Patent application No. 60/939,432 filed by Farhan and Peifer on May 22, 2007 and incorporated herein by reference.

BACKGROUND OF THE INVENTION

The present invention relates to a health or wellness monitoring system and apparatus, where the apparatus employs a universally accessible interface for people without or with disabilities, capable of performing a myriad of health monitoring features. The universally accessible apparatus is also used in a system to provide two-way communications between remote caregivers and care recipients who need some assistance to remain independent. Embodiments of the present invention also describe a novel activity monitoring of a person needing care by use of motion sensing and time based statistical behavior analysis.

DESCRIPTION OF THE RELATED ART

There are several patents and applications that describe systems and methods that are used to perform some form of self-care or health monitoring functions, however, a typical shortcoming of the current state of the art is that it fails to address the needs of people with disabilities or people who are aging into disability. These references fail to elaborate and define the necessary interface requirements to be useable by these people. For example, US Publication Number 2004/0249250 filed in the name of McGee teaches a system and apparatus for monitoring and prompting medical self-care events and communicating medical information to the patient's caregivers using a server in communication with a device via the Internet, phone or wireless. The system of McGee further comprises requesting specific reports, prompting and displaying patient self-care events without defining the user interface thus requiring that a person must have computer experience and high level hand-eye coordination skills. The user prompts and events include ordinary and obvious tasks such as taking medications, monitoring blood pressure, blood glucose, weight, temperature, blood oxygen level, EKG etc. and for reporting self-care behavior and health status, and alerts to the patient's caregivers through email, web browser, fax, and/or telephone (including text and voice formats) as well as request the automatic receipt of reports at specified time intervals. Alternatively, the remote device may be a personal computer. Ordinary personal computers are inadequate to serve as an effective communication tool for the many people who lack computer skills or have some form of disability (from here on defined as People With or Aging Into Disability, PWAID). McGee fails to address the user interface requirements of such people. Furthermore, the conventional personal computer mouse fails to be useful for many people with visual impairment or those with limited manual dexterity.

The current art references also fall short in addressing the need for communication for PWAID. In all the current art references the typical method of communication to the patient is by asserting a prompt, without considering the needs of the care recipient requesting some form of action or information to be transferred back to the central server or database or caregiver. The current art does not define a means to communicate information in a fashion that would be accessible to many of the people who need assistance to remain independent. Prior art thus assumes that the user is quite capable of using an ordinary computer to get health information, instructions on how to use medical devices, email, or text messages.

One embodiment of the present invention introduces a novel scheme to monitor activity around a motion sensor that can be enhanced by feedback from the care recipient. This embodiment of the present invention also considers the fact that the PWAID care recipient may not be the only moving object within the proximity of the sensor. In the above cited references there is no consideration given for situations where more than one being or moving object may be present in front of the motion sensor thus rendering them only useful to a very narrow set of cases. Also, these references still require the intervention of an external observer to train the system. U.S. Pat. No. 7,002,463 awarded to Wakabayashi teaches a system and apparatus for determining abnormalities in daily activity patterns and includes databases for storing activity data from the sensors, a statistical analysis section, an abnormality determination section, an evaluation section and a notification section. However, at the end an external observer's intervention is required to close the feedback loop back to the device to determine the optimum patient motion signature, forcing it to fall short of being automatic and thus fails the purpose. Wakabayahsi also falls short of addressing very common situations where more than one moving object is present in front of a given motion sensor. These systems would yield erroneous results when more than the intended patient is moving around the household, such as the common situation where a pet or visitors are present.

BRIEF SUMMARY OF THE INVENTION

One embodiment of the present invention, can be implemented within a system comprising a set of apparatuses or home appliances and a computer server, where the system allows a set of remote caregivers (informal or professional) to communicate, monitor and assist a set of care recipients, where each care recipient is located near the apparatus, and generally wants to remain independent but needs some assistance to maintain wellness and to avoid social isolation. The system allows caregivers to send email and text messages, medical lists, reminders, calendar events, and photos over the internet to the care recipient via this apparatus. The apparatus may contain, as a non-limiting example a processor, microphone, speaker, display, serial and USB ports, as well as a Passive Infra-Red motion sensor. The apparatus is typically always on and operates in secure communication with the server computer over the internet to provide the care recipient two-way communication, wellness monitoring and management and activity monitoring. The apparatus has mechanical and other features especially suitable for people with disabilities or people who may be aging into disability with changes in mobility, vision, hearing, or cognitive abilities, hereinafter referred to as PWAID (People With or Aging Into Disability). Specifically, the apparatus possesses a custom rotary knob or other similar interface along with a custom graphical and audible human interface that render embodiments of the present invention suitable for universal use, including for the PWAID. The apparatus also has features necessary to communicate with wired or wireless devices. The devices include commercially and conventionally available health and wellness measurement devices as well as wireless home appliances including but not limited to motion sensors, door switches and wireless fall detector pendants, as well as alternative interface assistive technology devices such as a sip and puff controller for people who cannot use their hands.

The use of the rotary knob provides for a singular, stationary, easy to find, learn and operate input interface suitable for the visually and mobility impaired. The rotary knob is integrated with the system software so as to provide audio, visual, and tactile feedback as the user rotates the knob and navigates and selects options. The PWAID care recipient hence is not expected to or required to have any conventional computer knowledge.

The user interface consists of a set of nested circularly positioned icons that can optionally become earcons, restricting the user only to three choices: turn the knob clockwise, turn the knob counterclockwise and thirdly press (depress) the knob. This simple interface, unlike conventional mouse operated computer interfaces, reduces the possibility for the user to make a mistake and makes it easy to navigate back to the starting point. Also, at every circularly positioned icon screen, a Home icon and a Help icon exists. Due to the circular nature of design of the screen, the PWAID user will be able to easily and predictably return to the Home icon and thus allow an easy return to the Home screen.

Also according to an embodiment of the present invention, an activity monitoring scheme is presented that uses a Passive Infra-Red motion detector capable of detecting human-only motion and speed. The scheme further employs an algorithm that works as follows:

Step 1: Determine the average motion speed of human-only object and from here accept a range of motion speeds that are not a statistically unusual percentage above or below of the mean speed.

Step 2: For a given period, such as, several days to several weeks known as the statistical processing phase, and for every interval, less than or equal to an hour and over a full twenty-four hour day, compute the mean and standard deviation for the motion counts that meet the speed range of Step 1.

Step 3. In the operational period that follows the statistical processing of Step 2, where for every interval similar to Step 2, the number of motion events that meet the speed criteria of Step 1 are counted, the zero counts are not used and the non-zero counts are compared to a statistical function using the statistics calculated for every interval derived from Step 2. The said statistical function will define the expected normal count for every interval and will determine an above normal, normal, below normal or Zero-activity for each observed interval.

Step 4. Continue to compute mean and standard deviation of the non-zero counts for each hourly or sub-hourly interval and for a period greater than several days and replace the previously computed mean and standard deviation values for each, if and only if this option is selected by the remote caregiver or by the PWAID care recipient.

DETAILED DESCRIPTION OF THE INVENTION

Figure 1:
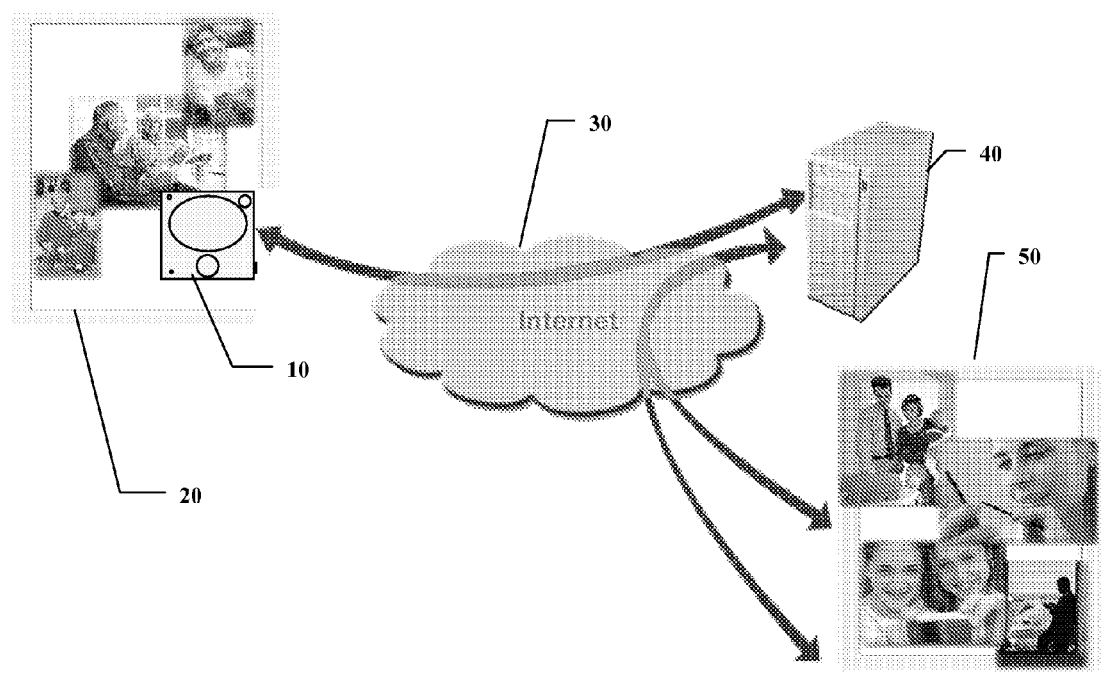
FIG. 1 is the network view of an embodiment of the invention depicting the Caregivers on right hand side connected to the server via internet, and the care recipients shown on the left hand side next to the Apparatus, where Apparatus is connected only to the server via Internet
Figure 2:
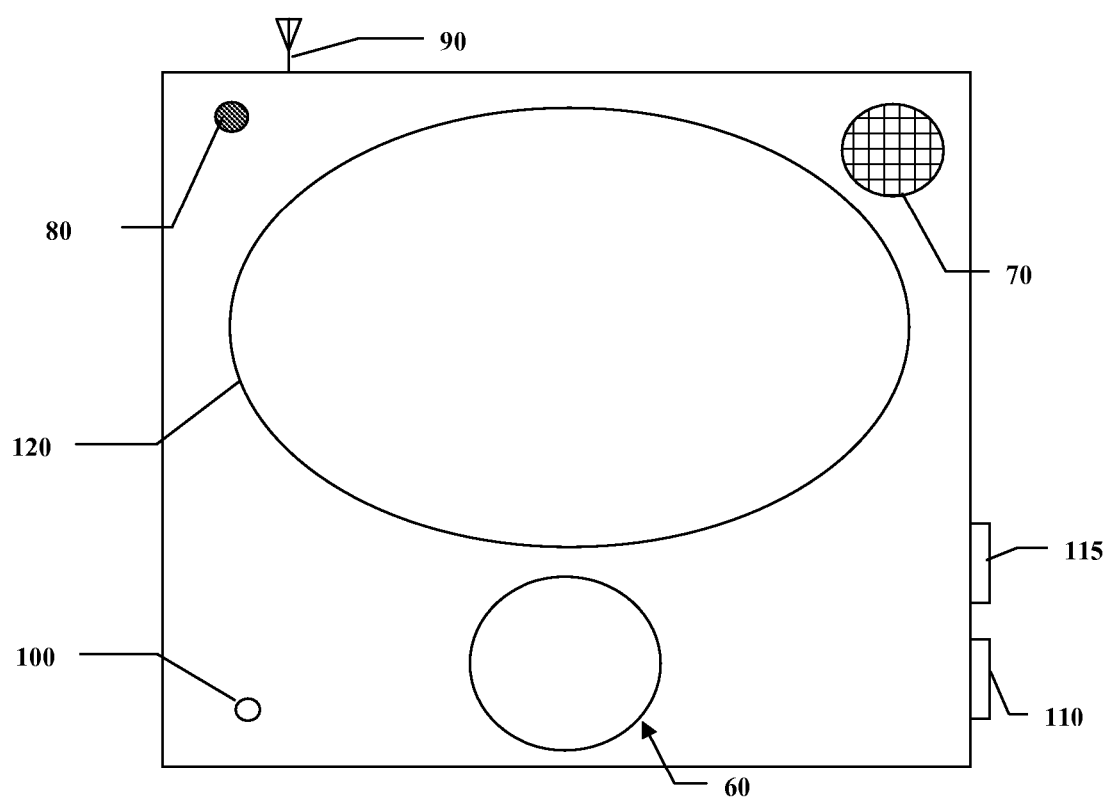
FIG. 2 is a detailed front view of apparatus part of an embodiment of the invention

Embodiments of the present invention establish a network connection between remote caregivers 50 and care recipients 20 through a secure database and web server 40 over the Internet 30. The network is accessed by the apparatus 10 in the recipient's home. Caregivers connect to the system via 40 and through standard Internet browsers, cell phones, email, and mobile communication devices.

The apparatus in the recipient's home, running an embedded control software, includes: a graphical display (item 120) to present visual representations of the system options; an audio speaker (item 70) to produce speech and non-verbal sounds to communicate with and alert the recipient; a microphone (item 100) for recording human speech and ambient sounds; Passive Infra-Red motion detector (item 80) to detect human-only movements also capable of measuring motion speed around the apparatus; a wireless transmitter and receiver 90 to communicate with wireless devices, a rotary knob (item 60) that is used to navigate through system options (by rotating) and to select or execute system options (by depressing the knob); access ports (item 115) for connecting to the internet as well as external medical monitoring devices; and optional memory expansion cards (item 116) that can be added to increase storage capacity for archiving data, pictures, and messages.

Figure 3:
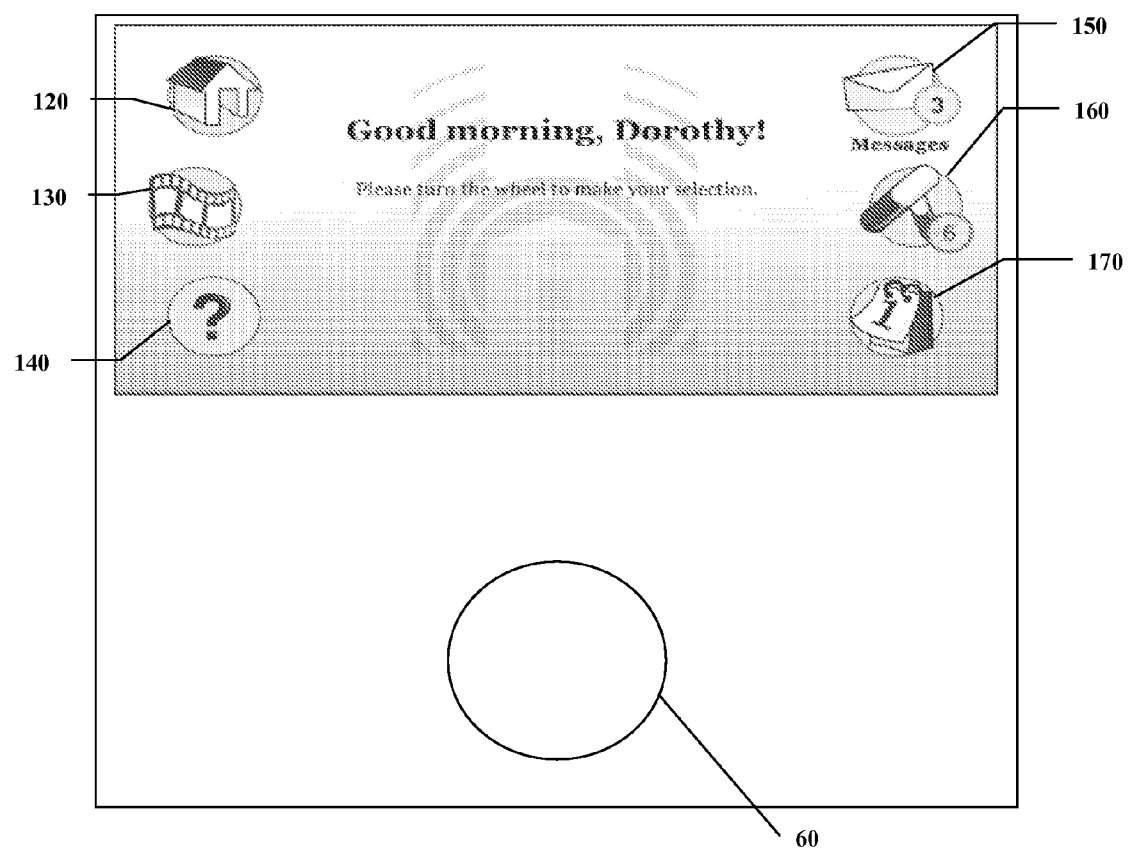
FIG. 3 is an example of the home screen, with icons forming a semi-circular fashion
Figure 4:
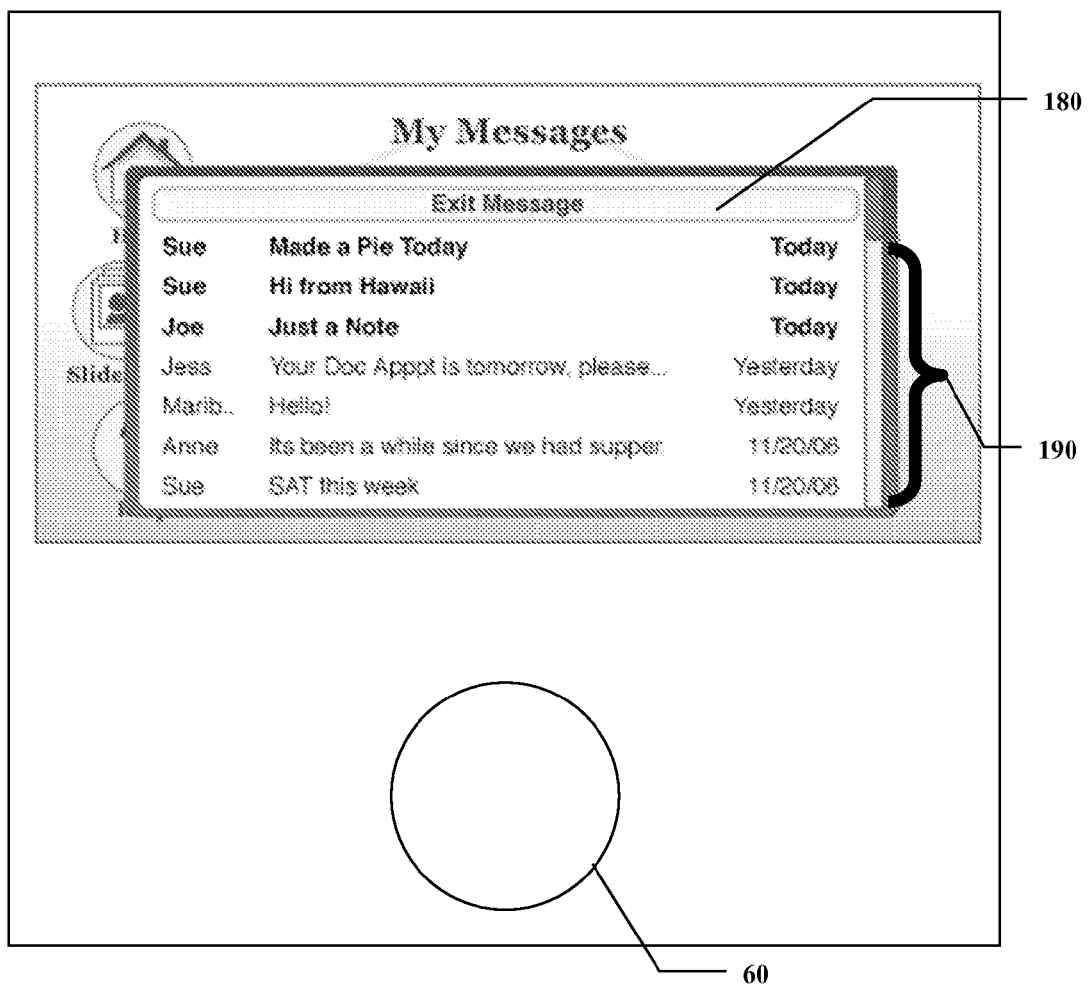
FIG. 4 is view of an example messages list where the top of the list begins and ends with an Exit List icon

A novel user interface, designed specifically for the apparatus, provides universal access and is easy to learn and easy to remember. The home screen, with icons forming a semi-circular arrangement, either in actual physical appearance or logically presented, presents options that the recipient can choose between. The recipient navigates through the system options by rotating the rotary knob, and the recipient selects (execute the option) by depressing the rotary knob. Starting from the upper left corner and rotating in clockwise order, the options presented in FIG. 3 include: Home 120, Messaging 150, Wellness 160, Calendar 170, Help 140, and Slideshow 130. Throughout all levels of the interface, whenever the user executes the Home icon the application always returns the user to this initial screen. In some embodiments, the rotary knob can be replaced by a joystick type interface allowing clockwise and counterclockwise movement with depressions or, simply left and right and/or up and down movements with depressions.

A message list is presented when the recipient selects the "Messages" option 150 from the "Home" screen. In the Message List, the top of the list begins and ends with an Exit List icon 180. The "My Messages" window partially covers graphical icons on main screen to provide more room to display longer message subjects, however, the partially visible graphical icons help remind users how to navigate. For message lists that are longer than can be displayed in one window, the user can scroll 190 through the rest of the list by rotating the rotary control knob 60.

Figure 5:
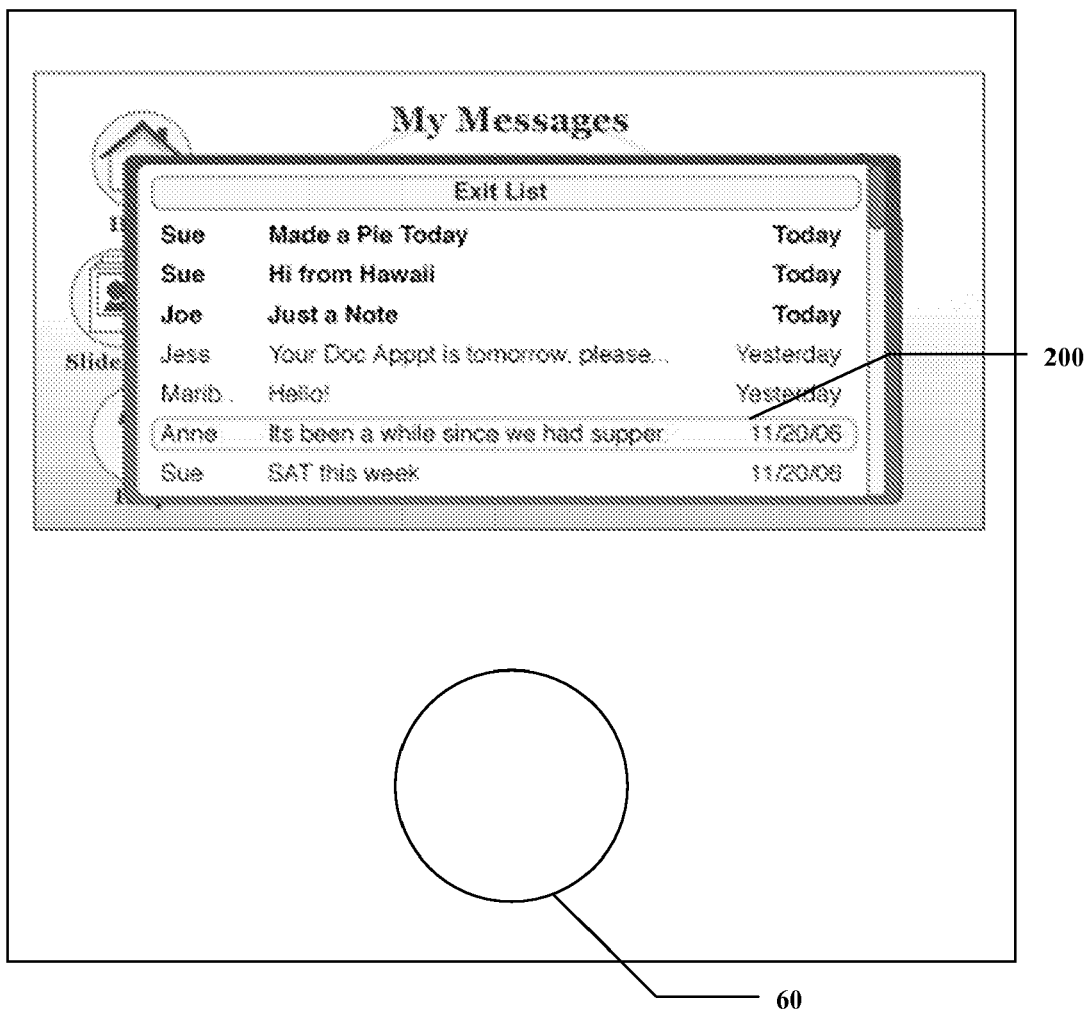
FIG. 5 shows a typical message list where the user has already scrolled down to the desired message

For each message on the message list, the illustrated embodiment lists the message author, the message title, and the date the message was sent. To open and read a particular message, the user actuates the interface, (i.e. rotates the knob) to scroll to the desired message, as for example item 200 in FIG. 5. With each step of rotation, the message in focus is highlighted in color (yellow for example in the illustration), and the user may receive audio (spoken or non-verbal tone) and/or tactile (rotary knob click) feedback that the message focus has changed. For blind or visually impaired recipients, the audio feedback can be configured to produce speech output reading the text displayed on the screen.

Figure 6:
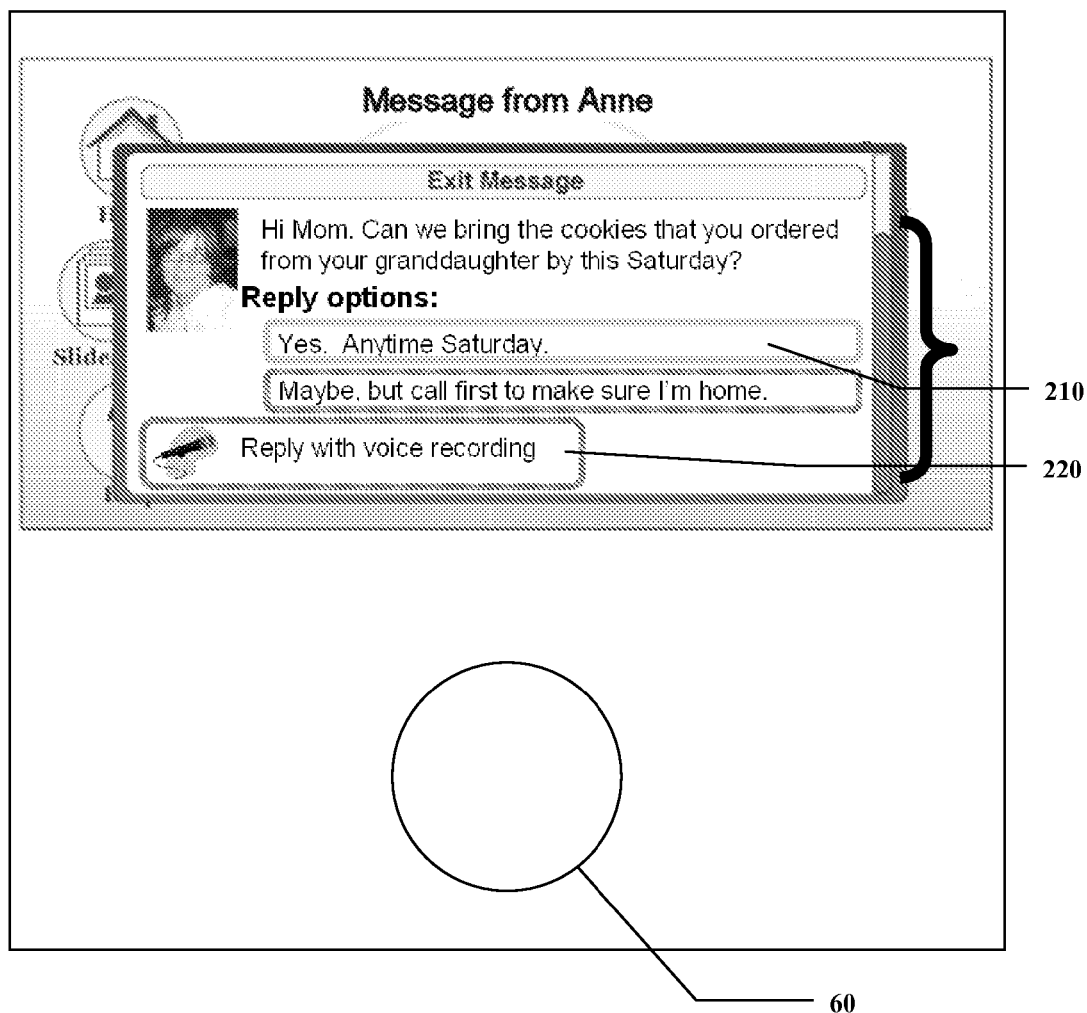
FIG. 6 is a view of the message content view with options to scroll through, exit, or respond to the message.
Figure 7:
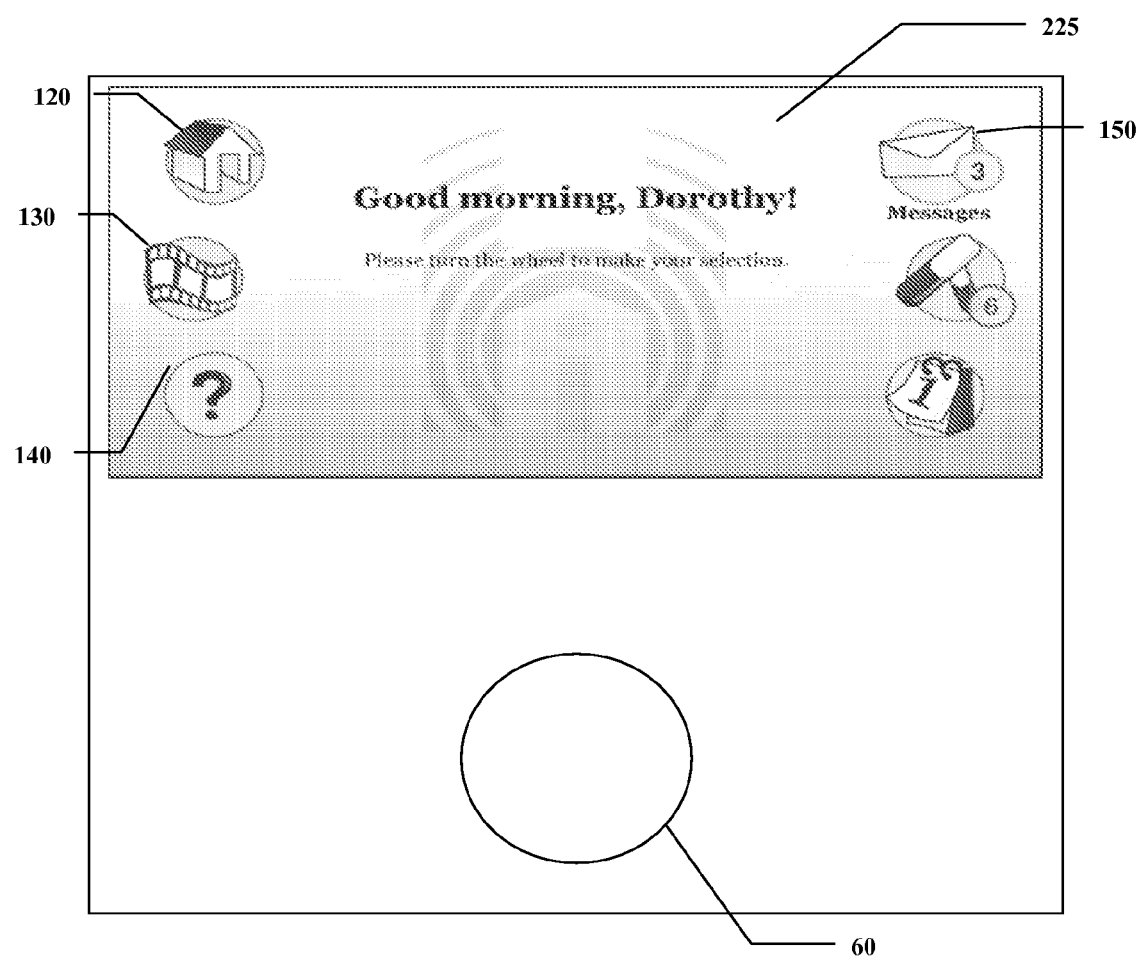
FIG. 7 is a view of the Home screen when user returns from reading a message

The message details are presented to the user when a particular message is selected from the list by depressing the knob when a message title (as in FIG. 5) was highlighted. The text content of the message is displayed on this screen, and blind or visually impaired recipients can configure the apparatus to produce audio speech output reading the contents of the text message. Options to exit or respond to the message are chosen by the user with the rotary knob 60. By rotating the knob, the option in focus is highlighted in color, and the user receives audio (spoken or non-verbal tone) and tactile (rotary knob click) feedback that the focus has changed. For blind or visually impaired recipients, the audio feedback can be configured to produce speech output reading the text displayed on the screen. The user selects an option by depressing the knob when the desired option is in focus. In the example in FIG. 6, the focus 210 is on one of the preprogrammed reply options that the caregiver created when sending the message. For every message, the user has the option to send a voice reply 220. As with every option in the system, the user executes this option by depressing the knob while it is in focus (highlighted).

After exiting the message list the application returns to the Home screen 225. If there are remaining messages that have not been read, the message icon 150 indicates the number of unread messages as a reminder to the recipient.

Figure 16:
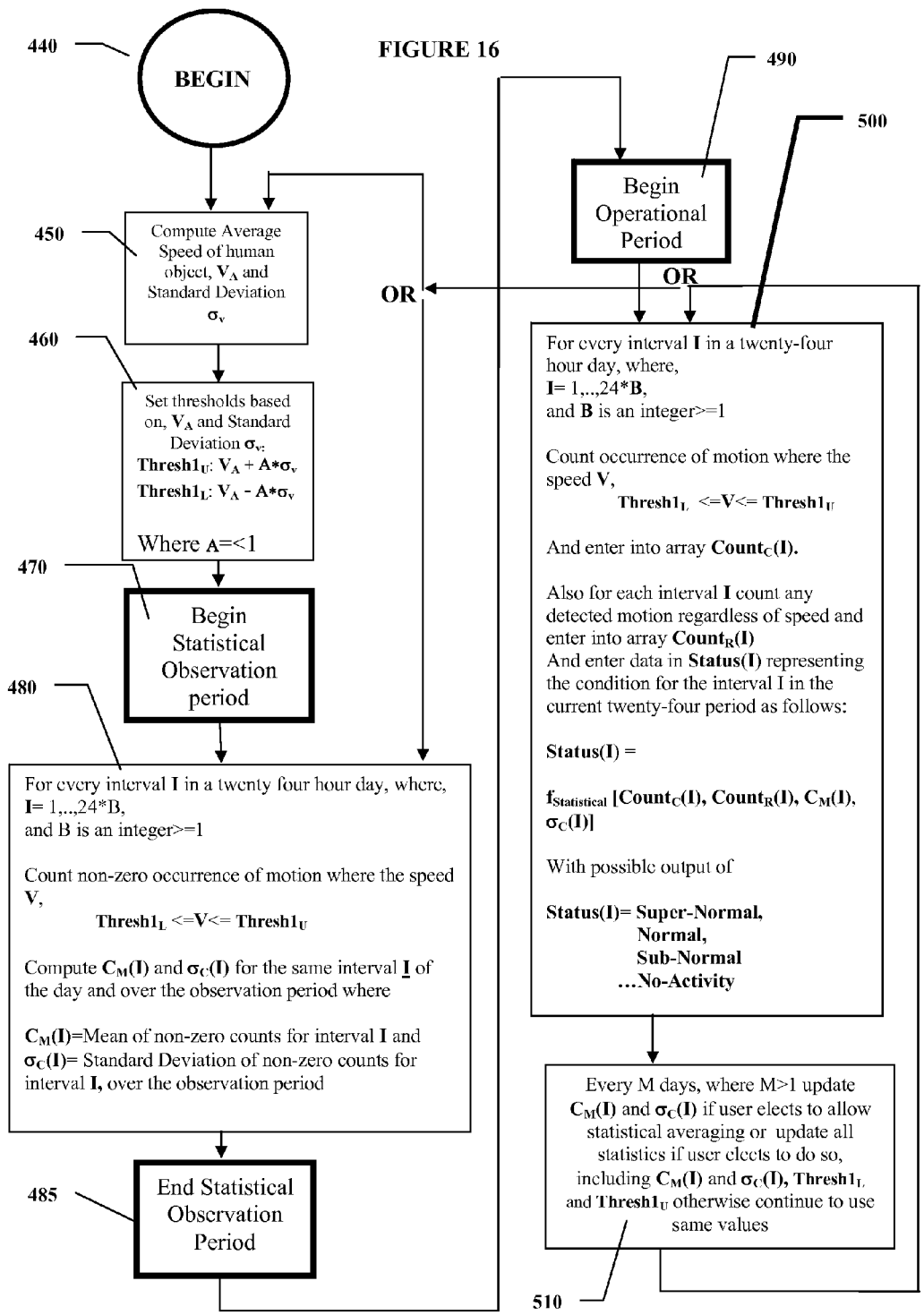
FIG. 16 is a view of an embodiment of the Activity Monitoring Algorithm

Embodiments of the present invention may include a set of health and wellness monitoring functions that promote self management by the recipient and enable remote assistance by the remote caregiver. The three basic categories of wellness functions include medication assistance, medical measurements, and activity monitoring. Without any interaction with the apparatus, the recipient will receive medication reminders that are displayed automatically (with visual and audio notification) when scheduled to appear by the caregiver. Also without any interaction with the apparatus, the recipient can take a variety of medical measurements (such as blood pressure, weight, glucose, heart rate, and oxygen saturation) using wireless home health monitoring devices, and the measurements from these external devices will be automatically be transferred to the apparatus where the data is stored and organized for the recipient and transferred to authorized remote caregivers. And also without any interaction with the apparatus, the system continuously monitors activity using the embedded motion sensor and statistical behavior analysis algorithms (FIG. 16).

While many of the wellness functions are supported automatically without requiring any interaction with the device, the recipient can also initiate measurements, review the medication list, respond to reminders, and examine all of the data by interacting with the user interface on the apparatus.

The recipient can also learn more about how to take measurements, and how to interpret the measurements and wellness information by using the Help function.

To interact with the Wellness functions, the recipient selects the Wellness option 160 from the Home screen by rotating and depressing the rotary knob 60. At this interface level, a subset of three wellness options is presented: medication assistance 230, measurements 240, and activity 250. In the example in FIG. 8, the Medication wellness option (item 230) is in focus as indicated by the highlighted color. As with every option in the system, the user executes this option by depressing the knob while it is in focus (highlighted).

The Medication list is presented after the Medications option (item 230 in FIG. 8) is selected by depressing the rotary knob. The Medication list provides a summary of the current medications used by the recipient. The list is created and maintained by the caregiver on the caregiver website, but the recipient is encouraged to review the list whenever they are uncertain about their medication schedule. The user can scroll (as in 260) through a longer list than can be displayed on one screen by rotating the rotary knob. With each step of rotation, the medication in focus is highlighted in color (see 270 for the Lipitor example highlighted in yellow), and the user receives audio (spoken or non-verbal tone) and tactile (rotary knob click) feedback that the focus has changed. For blind or visually impaired recipients, the audio feedback can be configured to produce speech output reading the text displayed on the screen. The user can get additional information about any medication on the list by depressing the rotary knob while the medication in focus. To exit this screen, the user can let the system time out and it will automatically return to the Home screen, or the user can rotate to the "Exit Medication List" option 280 and depress the rotary knob.

Figure 8:
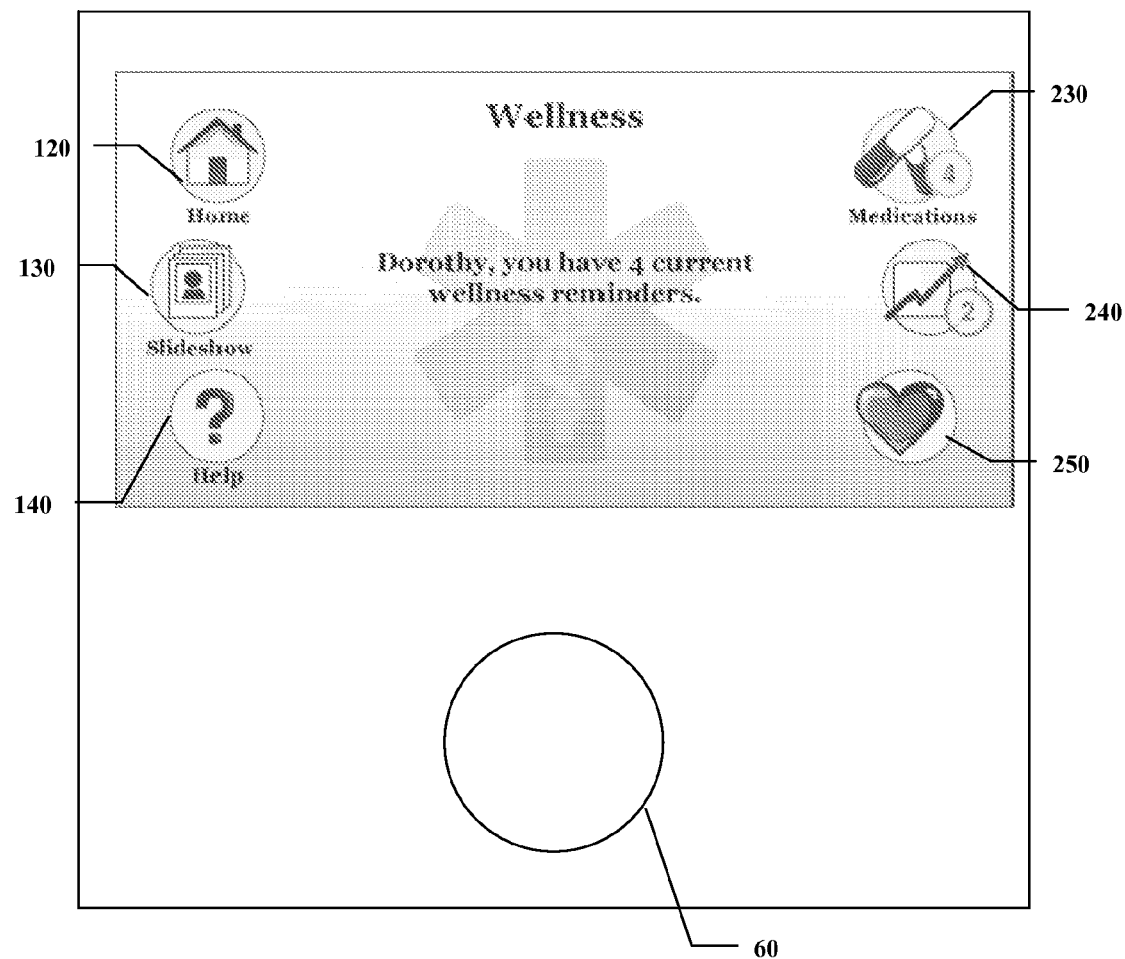
FIG. 8 is a view of the Wellness screen that is presented after icon 160 (Wellness icon) is pressed in FIG. 7.
Figure 9:
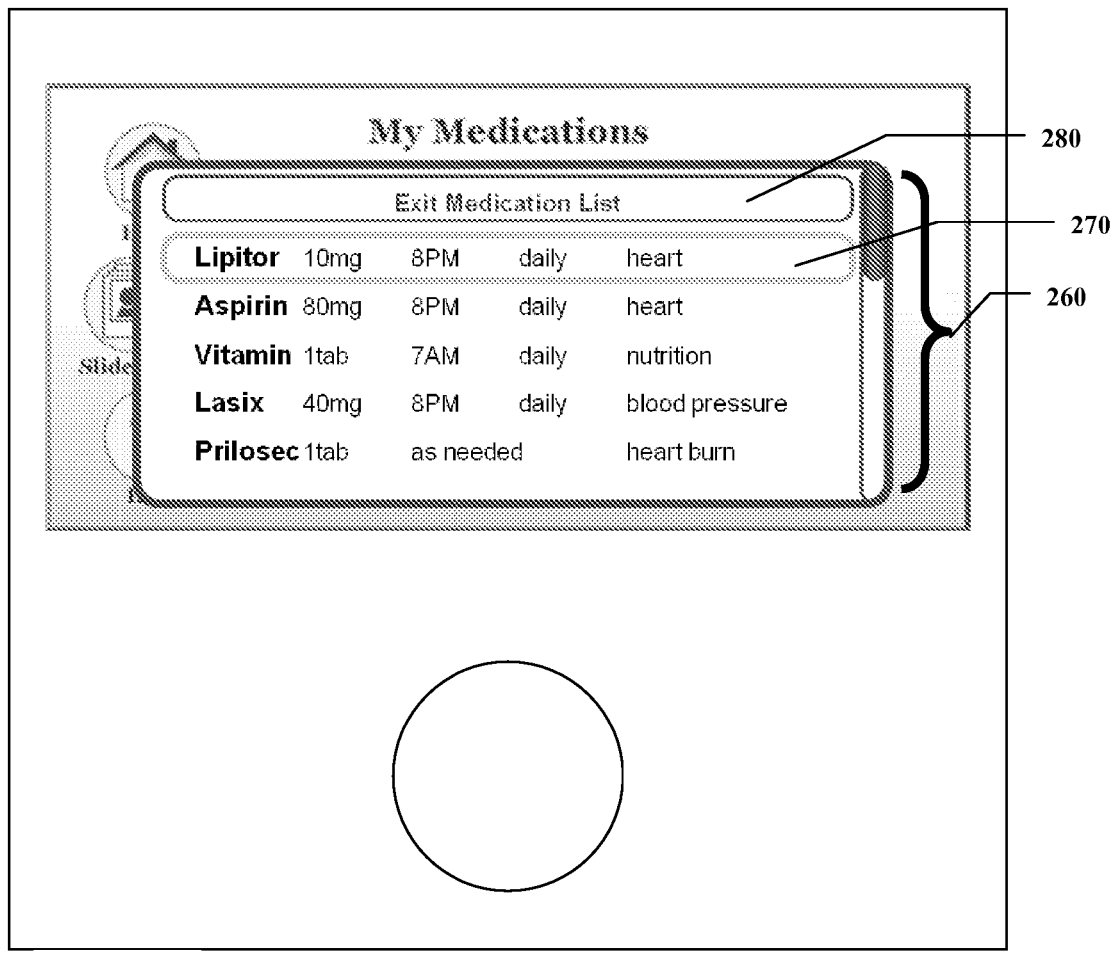
FIG. 9 is a view of the Medication list that is presented after icon 230 (Medications icon) is pressed in FIG. 8.

The recipient can initiate or review their customized Health Measurement list by rotating to and depressing the knob when the "Measurement" icon (240 in FIG. 8). The Measurement list provides a summary of the current measurements that the recipient is scheduled to perform on a regular basis. The list is created and maintained by the caregiver on the caregiver website, and the recipient is encouraged to review the list whenever they are uncertain about their measurement instructions or schedule. The user can scroll (as in 290) through a longer list than can be displayed on one screen by rotating the rotary knob. With each step of rotation, the measurement option in focus is highlighted in color (see 300 for the Blood Pressure example highlighted in yellow), and the user receives audio (spoken or non-verbal tone) and tactile (rotary knob click) feedback that the focus has changed. For blind or visually impaired recipients, the audio feedback can be configured to produce speech output reading the text displayed on the screen. The user can get additional information about any measurement on the list by depressing the rotary knob while that particular measurement option is in focus. To exit this screen, the user can let the system time out, and it will automatically return to the Home screen; or the user can rotate to the "Exit Measurement List" and depress the rotary knob.

Figure 10:
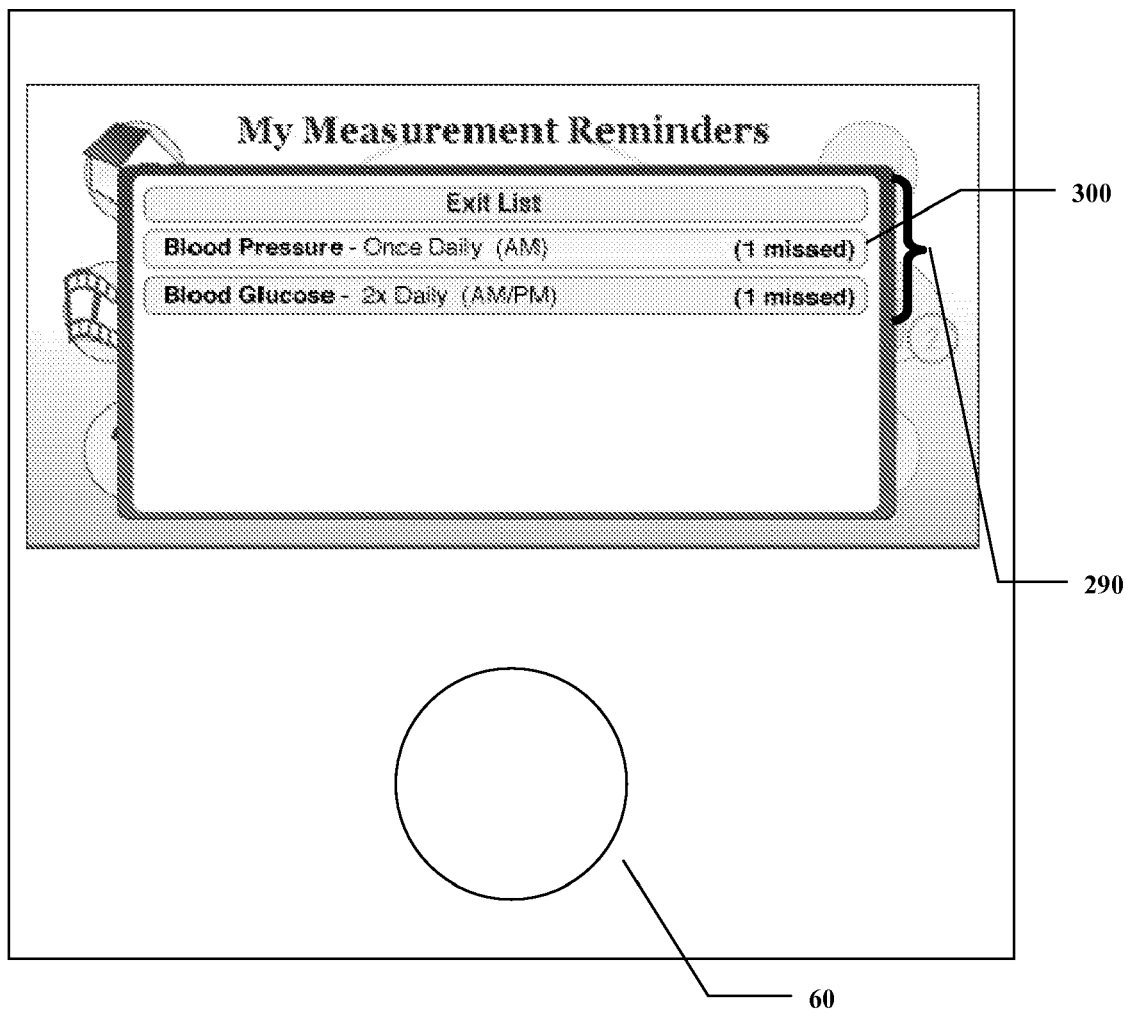
FIG. 10 is a view of the Measurement screen that is presented after icon 240 (Health Measurement icon) is pressed in FIG. 8.
Figure 11:
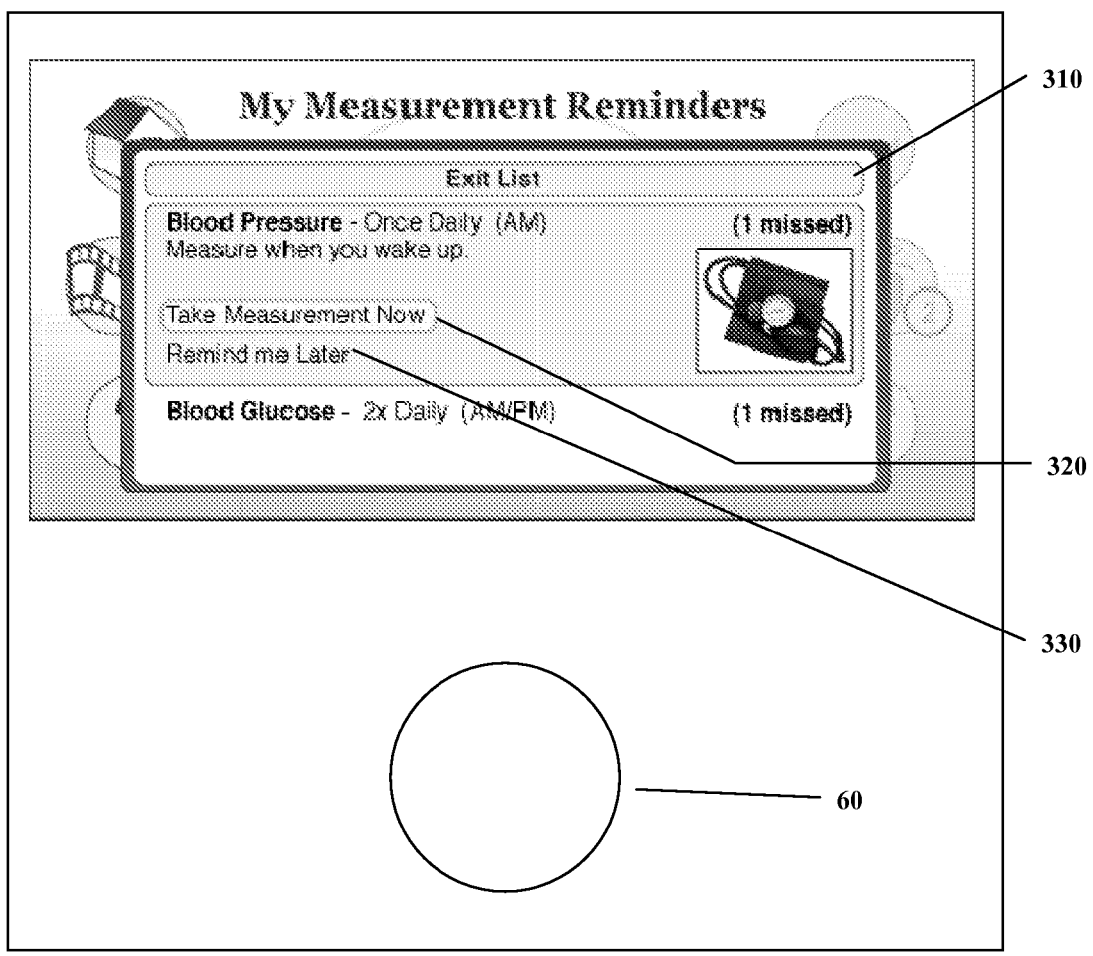
FIG. 11 is a view of the Measurement details screen that is presented after icon 300 (Blood Pressure Measurement icon) is pressed in FIG. 10.

Details for a particular measurement type can be selected from the list by depressing the knob when a measurement option on the list (item 300 is Blood Pressure Measurement example in FIG. 10) is highlighted. In FIG. 11, the screen illustrates the options to "Take Measurement Now" (item 320), "Remind me Later" (item 330), or "Exit Measurement List" (item 310) that are displayed on this screen. Blind or visually impaired recipients can configure the apparatus to produce audio speech output reading the text contents of the measurement options. Options to exit or respond to the measurement reminders are chosen by the user with the rotary knob 60. By rotating the knob, the option in focus is highlighted in color, and the user receives audio (spoken or non-verbal tone) and tactile (rotary knob click) feedback that the focus has changed. For blind or visually impaired recipients, the audio feedback can be configured to produce speech output reading the text displayed on the screen. The user selects an option by depressing the knob when the desired option is in focus.

Figure 12:
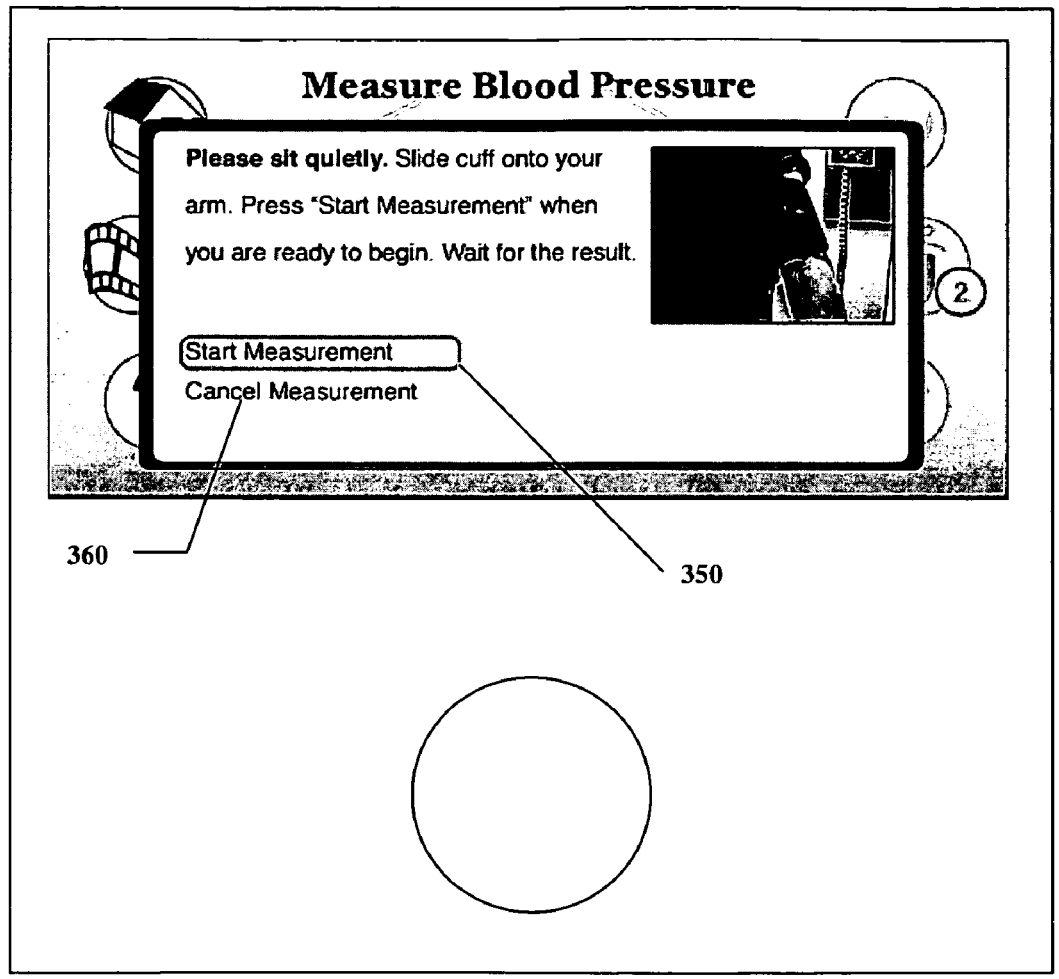
FIG. 12 is a view of the Measure Blood Pressure screen that is presented after icon 320 (Take Measurement Now) is pressed in FIG. 11.

FIG. 12 is a view of the details to initiate a particular measurement type. This interface level is arrived at by depressing the knob when the "Take Measurement Now" option (item 320 is Blood Pressure Measurement example in FIG. 11) was highlighted. FIG. 12 illustrates the options to "Start Measurement" (item 350) or "Cancel Measurement" (item 360) that are displayed on this screen. Blind or visually impaired recipients can configure the apparatus to produce audio speech output reading the text contents of the measurement options. Options to start or cancel are chosen by the user with the rotary knob 60. By rotating the knob, the option in focus is highlighted in color, and the user receives audio (spoken or non-verbal tone) and tactile (rotary knob click) feedback that the focus has changed. The user selects an option by depressing the knob when the desired option is in focus.

Figure 13:
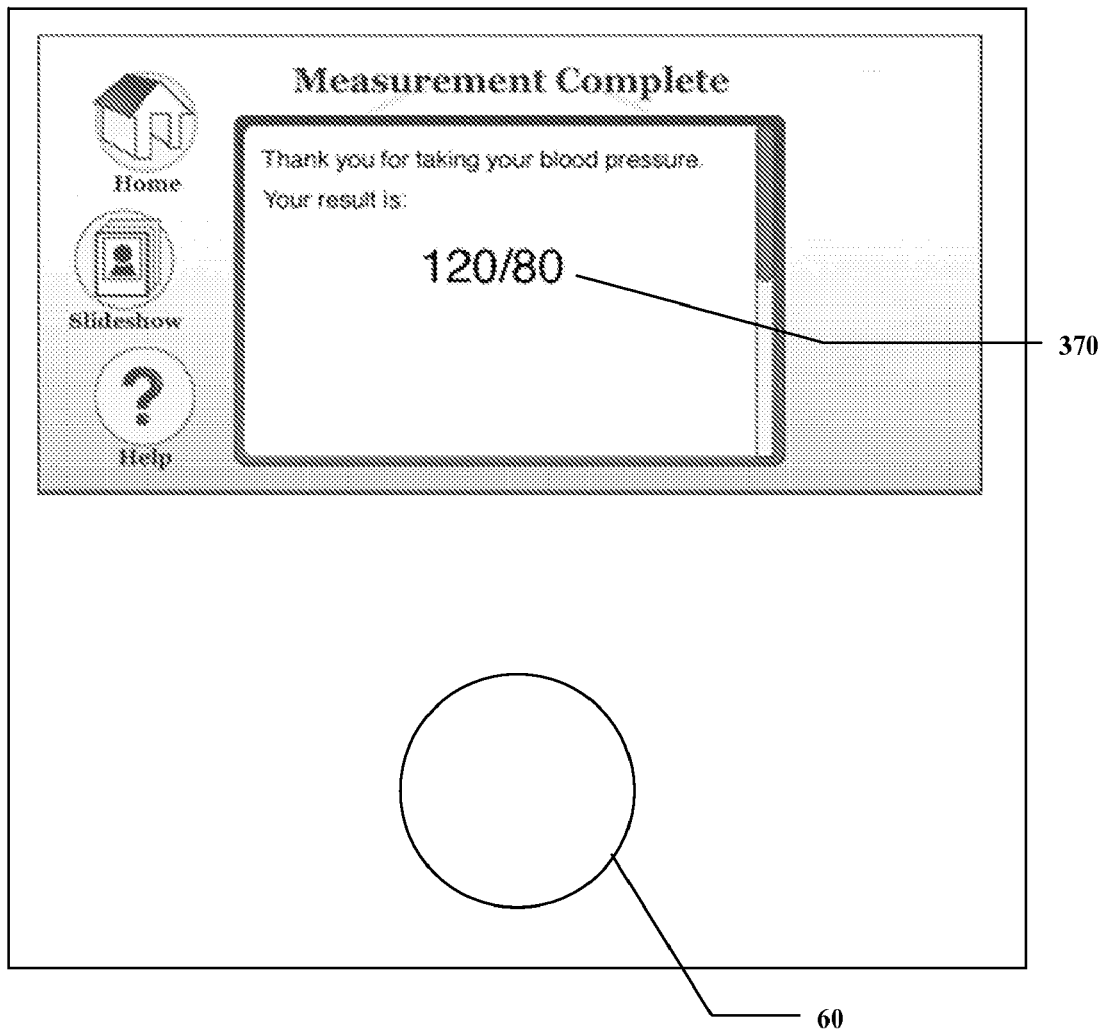
FIG. 13 is a view of the Measurement Completed screen that is presented after a measurement is made and the data have been transferred from the external medical device to the apparatus through either a wired or wireless connection.

When measurements are completed, the data are transferred and displayed for the recipient. The example in FIG. 13 displays the numeric value of the Blood Pressure measurement (item 370). Blind or visually impaired recipients can configure the apparatus to produce audio speech output reading the value of the measurement.

Figure 14:
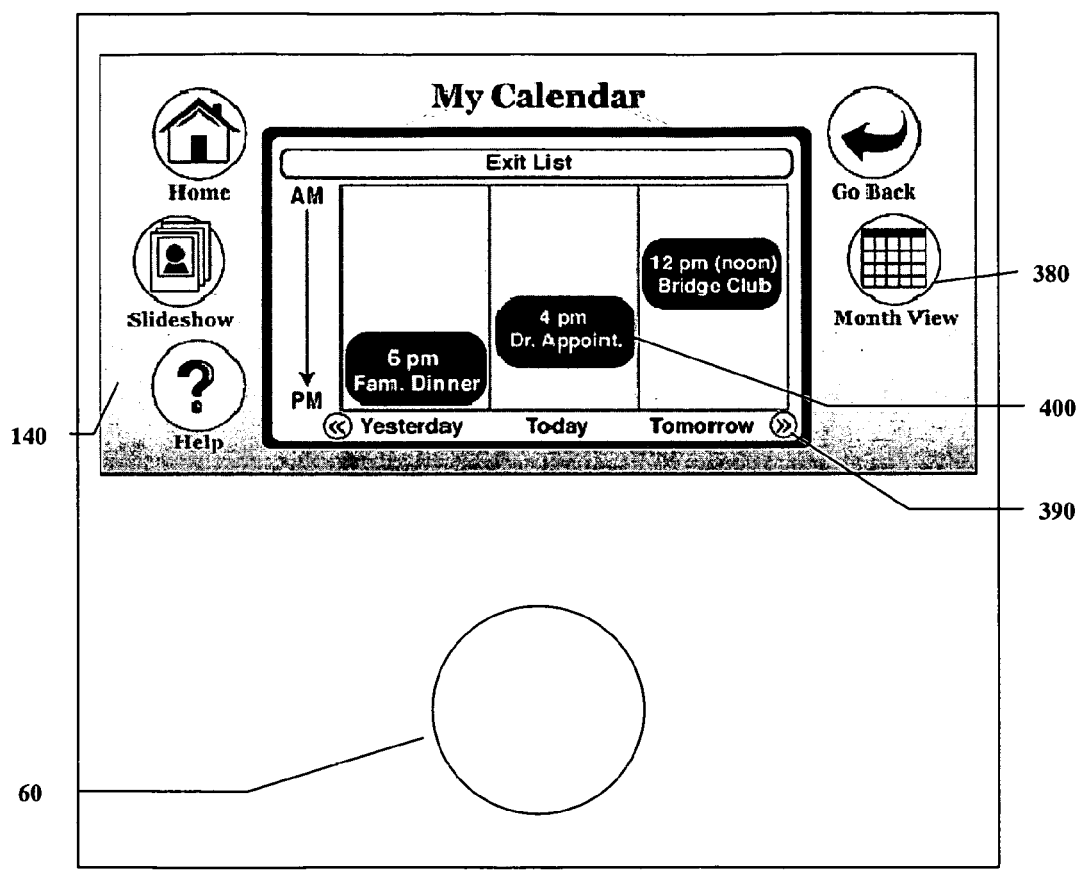
FIG. 14 is a view of the Calendar screen that is presented after icon 170 (My Calendar) is pressed on the Home screen (see FIG. 3).

An embodiment of the present invention includes an electronic calendar option that allows remote caregivers to schedule events and send event reminders to the care recipient. Without any interaction with the apparatus, the recipient will receive calendar event reminders that are displayed automatically (with visual and audio notification) when scheduled to appear by the caregiver. However, the recipient can review and respond to the list of scheduled calendar events by interacting with the user interface on the apparatus. As illustrated by item 170 in FIG. 3, the recipient can initiate the calendar options with the rotary knob control from the Home screen. In the example in FIG. 14, calendar events, such as the doctor appointment at 4 PM (item 400), are displayed for the current day. A variety of options are available to review event details, events from yesterday, events coming up tomorrow (item 390), and an option to see all the days with events in a month-at-a-time view (item 380). The event viewing options can be scrolled through with the rotary knob, and as each option comes into focus there is visual (indicated by the highlighted color), audio, and tactile feedback. As with every option in the system, the user executes the calendar options by depressing the knob while it is in focus (highlighted). Blind or visually impaired recipients can configure the apparatus to produce audio speech output reading the calendar events and describing the response options.

Figure 15:
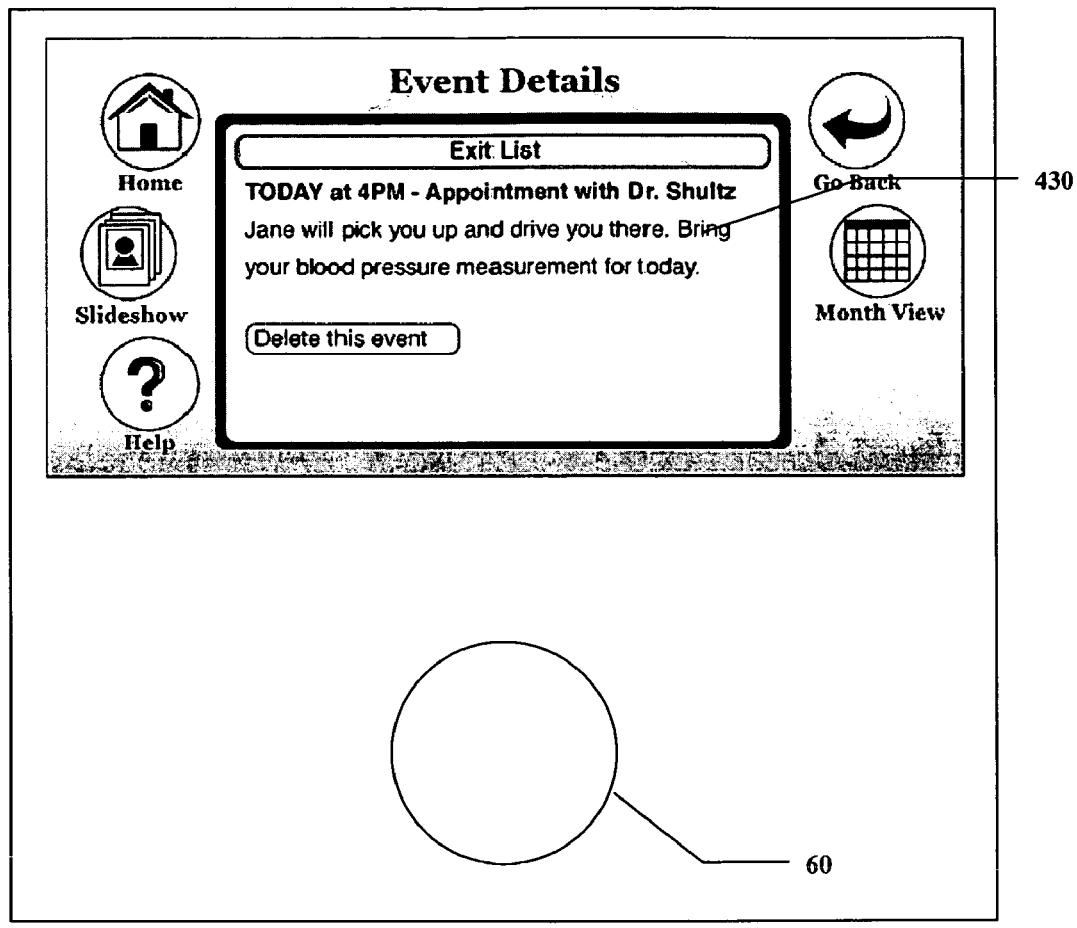
FIG. 15 is a view of the Calendar Event Details screen that is presented after icon 400 (4:00 pm current day appointment icon) is pressed in FIG. 14.

The details of a specific calendar event are displayed in text (item 430) on a new screen (FIG. 15) that is presented when the doctor appointment event (item 400 in FIG. 14) is selected by the user with the rotary knob (rotated to highlight and then pressed to execute). Users who are blind or visually impaired can configure the apparatus to produce audio speech output reading the text contents of the calendar event as well as the options to respond.

The Passive Infra-Red (PIR) motion detector 80 is a conventionally available detector capable of detecting human size thermal profiles, hence avoiding false sensing of pets and other small thermally radiant objects. This PIR 80 is also capable of measuring the speed of a moving human object that crosses its Infra-Red detector beam. This is done simply by measuring the rate of change of detected thermal energy. The rate of change of the current output of the PIR detector is proportional to the rate of change of detected thermal energy. Therefore by measuring the rate of change of the instantaneous detector output current as well as the total current, one can measure speed of detectable motion. This PIR (80) thus prevents false detection of pets and also allows for accepting motion counts based on an acceptable range of motion speed.

The algorithm 440 of FIG. 16 is described here in detail. The purpose of this algorithm is to observe the motion activity of a human object over an arbitrary amount of time in order to collect statistics, followed by an operational period where the motion activity of a human object is compared to the previously calculated statistics. During the operational period the decisions are made to determine the status of a human object. The algorithm of FIG. 16 starts by measuring the average speed and standard deviation of the speed samples over a number of measurements. This is done in step 450. In step 460, two thresholds are calculated. In one embodiment of the invention the thresholds are calculated as $Thresh1_U=V_A+A*\sigma_v$ and $Thresh1_L=V_A-A*\sigma_v$ where $Thresh1_U$ is the upper threshold, $Thresh1_L$ is the lower threshold, $V_A$ is the average or statistical mean of the samples of the motion speed and $\pi_v$ is the standard deviation of the distribution of the motion speed samples. A is a real constant less than or equal to 1.

Once step 450 is accomplished then the Statistical Observation of the human object begins with 470. Following 470, is step 480 where statistical observation of the human object is accomplished over an arbitrary several day observation period as follows: 1) The twenty hour period is broken up into 24*B, intervals, where B is an integer greater than or equal to 1. 2) For each interval of the twenty-hour day and for everyday over the course of the observation period, count the number of non-zero occurrences of a human motion where speed V falls within the range of $Thresh1_L$ and $Thresh1_U$. In other words anytime the speed of the observed motion V, $$Thresh1_L<=V<=Thresh1_U$$

increment the count for that day and for that interval. Continue to collect counts for each interval and for each day as defined above until the end of the observation period 485. At the conclusion of the observation period 485 compute $C_M(I)$ and $\sigma_C(I)$ for the same interval $\underline{I}$ of the day and over the observation period where $C_M(I)$=Mean of non-zero counts distribution for interval I and over the observation period $\sigma_C(I)$=Standard Deviation of non-zero counts distribution for interval I, over the observation period Once the statistical observation period is completed 485, the operational period of 490 begins. During step 500, the motion of the human object is observed and two counts for each interval I of the twenty-hour day where I=1, . . . , 24*B is made as follows:

Count occurrences of motion where the associated speed of that motion V, $$\text{Thresh1}_L <= V <= \text{Thresh1}_U$$

And enter into array $\text{Count}_C(I)$.

Also for each interval I count any detected motion regardless of speed and enter into array $\text{Count}_R(I)$. From here an arbitrary statistical observation function $f_{Statistical}$ is defined which uses $\text{Count}_C(I)$, $\text{Count}_R(I)$, $C_M(I)$, $\sigma_C(I)$ as inputs, so it has the general form of $f_{Staatistacal}[\text{Count}_C(I), \text{Count}_R(I), C_M(I), \sigma_C(I)]$ with only four possible outcomes for every interval I and those are: Super-normal (above normal), Normal, Sub-normal (or below normal) or No-activity. The results of $f_{SStatistical}[I]$ is then stored in array Status(I) therefore:

$$\text{Status}(I) = f_{Statistical}[\text{Count}_c(I), \text{Count}_R(I), C_M(I), \sigma_C(I)]$$

With possible values of
Status(I)=Super-Normal,
  Normal,
  Sub-Normal
  . . . No-Activity In step 510, every M days, where M>1 and is a number selected as an option, by an authorized observing user, the statistics of 480 can be updated and fed back to 500. Yet as another selectable option, calculations of step 450 and 460 can be updated as well. In other words is selected by the user the statistics of steps 450, 460 and 480 can be continuously updated.

What is claimed is:

1. A method for detecting human activity and providing time-stamp measurements but preventing false detections of pets, the method comprising the steps of:
   during a statistical observation phase:
      utilizing a monitoring device in proximity with a monitored human object, detecting motion and measuring motion velocity of the human object using a passive infra-red motion detector within the monitoring device for a minimum of P occurrences, where P is greater than 1, and wherein the passive infra-red motion detector only detects human sized thermal profiles, thereby detecting human-only motion;
      learning the motion speed of the human object by averaging the P measured motion occurrences and calculating a set of object detection thresholds based on this average;
      storing these object detection thresholds into a memory storage device within the monitoring device;
      utilizing the monitoring device, detecting subsequent human-only motion occurrences using the passive infra-red motion detector that fall within the above the set of object detection thresholds and capturing the time of day of such occurrence;
      a processor within the monitoring device performing statistical processing of these subsequent human-only motion occurrences over an initial statistical observation phase to determine counts of motion activity of the human-only object over a unit interval of time, less than or equal to an hour, and for every such interval within a twenty-four hour day;
      using the statistically processed occurrences from the statistical observation phase to define thresholds of normal activity for each of the unit intervals;
   during an operational period subsequent to the statistical processing phase:
      utilizing the monitoring device, detecting subsequent human-only motion occurrences after the initial statistical processing phase, that fall within the object detection thresholds above and counting these occurrences for every unit interval;
      the processor within the monitoring device performing decision making of normalcy by comparing the counts for each unit interval and comparing those to the levels computed during the statistical observation phase for each unit interval to determine user-defined normal, subnormal or no-activity status for the given interval for the current day and sounding an alert through a speaker of the monitoring device; and
      the processor within the monitoring device updating statistics by continuing to perform statistical processing of these motion counts for each unit interval to ensure that over time, the normal activity thresholds are statistically appropriate and if necessary updating the normal activity thresholds.

2. The method of claim 1, wherein during the statistical observation phase, further comprising the step of the processor within the monitoring device computing a mean and standard deviation for the observed counts for the given interval and setting an arbitrary threshold count for the given interval as a mathematical function of the mean and the standard deviation.

3. The method of claim 1, wherein the step of decision making of normalcy further comprises the processor within the monitoring device performing the step of deriving an output selected from the group of outputs including: above-normal, normal, below-normal or zero-activity, based on the inputs received for every interval within the twenty-four hour period, the inputs comprising a motion count for every occurrence of motion speed within the range learned during the learning step, a motion count of any motion event regardless of its speed, statistical mean computed for the interval and during the statistical processing phase, and standard deviation for the distribution for the said interval computed during the statistical processing phase.

4. The method of claim 1, wherein the step of updating statistics further comprises the processor within the monitoring device performing the step of computing the mean and standard deviation of each interval count over a minimum of a thirty interval period and updating the mean and standard deviation upon confirmation of a remote caregiver and hence computing and updating new thresholds for each interval.

* * * * *